United States Patent [19]

Kasai et al.

[11] Patent Number: 4,985,026

[45] Date of Patent: Jan. 15, 1991

[54] BLOOD COLLECTING TUBE

[75] Inventors: Masaaki Kasai; Sakae Yamazaki; Sanae Miyake, all of Yamanashi, Japan

[73] Assignee: Terumo Kabushiki Kaisha, Tokyo, Japan

[21] Appl. No.: 387,026

[22] Filed: Jul. 28, 1989

[30] Foreign Application Priority Data

Aug. 3, 1988 [JP] Japan ................................ 63-193608

[51] Int. Cl.[5] ................................................ A61B 19/00

[52] U.S. Cl. .................................... 604/403; 604/415; 128/760

[58] Field of Search ........................ 604/403, 415, 411; 128/760, 763, 764

[56] References Cited

U.S. PATENT DOCUMENTS

| | | | |
|---|---|---|---|
| 1,765,794 | 6/1930 | Hirth | 604/403 X |
| 3,975,350 | 8/1976 | Hudgin et al. | 604/57 X |
| 4,263,423 | 4/1981 | Schwindt et al. | 528/55 |
| 4,273,873 | 6/1981 | Sugitachi et al. | 623/66 X |
| 4,308,232 | 12/1981 | Crouther et al. | 604/403 X |
| 4,333,809 | 6/1982 | Schreckenberg et al. | 525/147 X |
| 4,378,435 | 3/1983 | Takagi et al. | 435/180 |
| 4,492,634 | 1/1985 | Villa-Real | 210/398 |
| 4,623,347 | 11/1986 | Kira | 623/1 |
| 4,856,533 | 8/1989 | Anraku et al. | 128/763 |

*Primary Examiner*—John D. Yasko
*Assistant Examiner*—Adam J. Cermak
*Attorney, Agent, or Firm*—Frishauf, Holtz, Goodman & Woodward

[57] ABSTRACT

A blood collecting tube comprises a tubular member made of synthetic resin which has an open end and a closed bottom, and a closure member which is for closing the open end of the tubular member and allows a puncture needle to pierce therethrough, the interior of said blood collecting tube being kept under reduced pressure, said tubular member being essentially made of a polyester resin mixture of a polyester resin mainly based on a ethylene glycol and terephthalic acid and a polyester resin mainly based on ethylene glycol and isopthalic acid. The tubular member of this blood collecting tube can be suitably made by injection molding and has high gas barrier properties so that the capability of collecting blood decreases little with time.

31 Claims, 1 Drawing Sheet

BLOOD COLLECTING TUBE

BACKGROUND OF THE INVENTION

This invention relates to a blood collecting tube for collecting a blood sample for use in various blood tests.

Various blood collectors have been in clinical laboratory tests such as biochemical examinations and serologic tests. Generally used blood collectors are of the type comprising a blood collecting tube whose interior is kept under reduced pressure, and a tube holder capable of receiving the blood collecting tube therein and provided with a puncture needle at the tip thereof. The blood collecting tube comprises a tubular member made of glass or synthetic resin which has an open end and a closed bottom, and a rubber plug for closing the open end of the tubular member.

A tubular member made of glass can maintain the reduced internal pressure thereof for a long time but it is easily damaged in transportation and operation. The resultant damaged tubular member causes the contamination of the blood sample in the tubular member. Additionally, a glass tubular member is relatively heavy to handle. In contrast to this, a plastic tubular member made of synthetic resin is advantageous because it is light and difficult to damage even when dropped.

A blood collecting tube using a conventional plastic tubular member has, however, the problem that the capability of collecting blood considerably decreases with time because of the insufficient gas-barrier properties of the tubular member. Although there is known a plastic tubular member made of polyethylene terephthalate, it is also disadvantageous because polyethylene terephthalate is easily whitens at the gate position upon injection molding and clogs the gate of the injection molding machine. It results in low productability.

SUMMARY OF THE INVENTION

Accordingly, it is an object of the present invention to provide a blood collecting tube comprising a tubular member which is made of synthetic resin having high gas-barrier properties so that the capability of collecting blood hardly decreases with time.

It is another object of the present invention to provide a blood collecting tube comprising a tubular member which is made of a synthetic resin suitable for injection molding.

According to an aspect of the present invention, a blood collecting tube comprises a tubular member made of synthetic resin which has an open end and a closed bottom, and a closure member which is for closing the open end of the tubular member and allows a puncture needle to pierce therethrough, the interior of said blood collecting tube being kept under reduced pressure, said tubular member being essentially made of a mixture of a polyester resin mainly based on ethylene glycol and terephthalic acid and a polyester resin mainly based on ethylene glycol and isophthalic acid.

BRIEF DESCRIPTION OF THE DRAWINGS

The above and other objects, features, and advantages of the present invention will be better understood from the following description taken in conjunction with the accompanying drawings, in which.

DETAILED DESCRIPTION OF THE PREFERRED EMBODIMENTS

Figure 1:
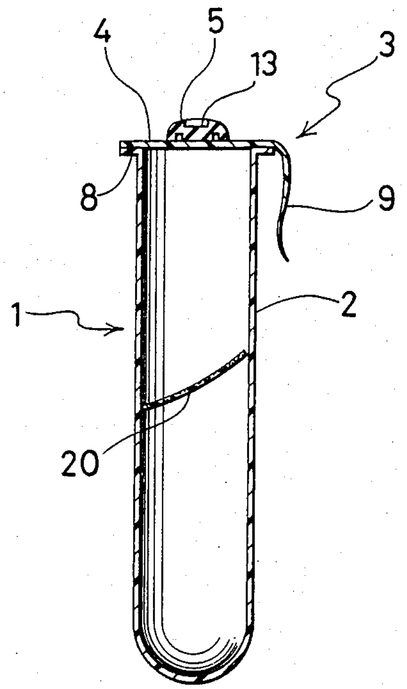
FIG. 1 is a cross sectional view of a blood collecting tube according to one preferred embodiment of the present invention.

Referring first to FIG. 1, a blood collecting tube 1 comprises a tubular member 2 which has an open end and a closed bottom, and a closure member 3 for closing the open end of the tubular member. The internal pressure of the blood collecting tube 1 is reduced in accordance with the amount of blood to be collected. The tubular member 2 is substantially cylindrical but for the region of its closed bottom. An annular outward flange 8 is formed at the open end of the tubular member 2. The flange 8 projects out perpendicularly to the axis of the tubular member 2 in order to mount a gas-barrier member of the closure member 3 as will be described later.

The tubular member 2 is made of a polyester resin mixture having high gas barrier properties to keep the interior of the blood collecting tube under reduced pressure. Specifically, it is essentially made of a polyester resin mixture of a polyester resin mainly based on ethylene glycol and terephthalic acid and a polyester resin mainly based on ethylene glycol and isophthalic acid.

The polyester resin mainly based on ethylene glycol and terephthalic acid in the present invention means a thermoplastic polyester resin which contains terephthalic acid components at a rate beyond 70 mol %, preferably more than 90 mol % of the whole dicarboxylic acid components, and ethylene glycol components at a rate beyond 70 mol %, preferably more than 90 mol % of the whole glycol components. The other part of the dicarboxylic acid components may be, for instance, an aromatic dicarboxylic acid such as isophthalic acid, diphenylether-4,4-dicarboxylic acid and naphthalene-1,4 (or 2,6)-dicarboxylic acid; an aliphatic dicarboxylic acid such as oxalic acid, succinic acid, adipic acid, sebacic acid and undeca-dicarboxylic acid; and hexahydroterephthalic acid. The other part of the glycol components may be, for instance, an aliphatic glycol such as propylene glycol, 1,4-butandiol and neopentyl glycol; cyclohexane dimethanol; and aromatic dihydroxy compounds such as bisphenol. So far as the rates of the terephthalic acid components and ethylene glycol components are within the above ranges, respectively, the resin may consist of a copolymer thereof or a mixture of polyethylene terephthalate (PET) and other polyesters polyester.

The molecular weight of the polyester resin mainly based on ethylene glycol and terephthalic acid according to the invention is not critical, though it should be within the range capable of forming the tubular member, of course. It may be specified by using its instrinstic viscosity ($\eta$) at 25° C. orthochlorophenol, which is generally more than 0.6 dl/g, preferably within the range of 0.8 to 0.85 dl/g.

The polyester resin mainly based on ethylene glycol and isophthalic acid in the present invention means a polyester copolymer which contains isophthalic acid components at a rate of 20 to 100 mol %, preferably 50 to 100 mol % of the whole dicarboxylic acid components; terephthalic acid components at a rate up to 80 mol %, preferably up to 50 mol % of the whole dicarboxylic acid components; ethylene glycol components at a rate of 10 to 95 mol %, preferably 15 to 90 mol %, more preferably 50 to 90 mol % of the whole dihydroxy compound components; and 1,3-bis(2-hydroxyethoxy)-benzene or 1,4-bis(hydroxyethoxy)benzene components at a rate of 5 to 90 mol %, preferably 10 to 85 mol %, more preferably 10 to 50 mol % of the whole dihydroxy compound components. If the rate of the isophthalic acid components is below 20 mol %, sufficient gas barrier properties of the tubular member cannot be obtained. If the rate of the 1,3-bis(2-hydroxyethoxy)benzene or 1,4-bis(hydroxyethoxy)benzene components is below 5 mol %, it is hard to restrain the generation of undesirable oligomers. If the rate of the 1,3-bis(2-hydroxyethoxy)benzene or 1,4-bis(hydroxyethoxy)benzene components is above 90 mol %, the rate of the polycondensation of the resin considerably decreases.

Also the molecular weight of the polyester resin mainly based on ethylene glycol and isophthalic acid according to the invention is not critical, though it should be also within the range capable of forming the tubular member. It may also be specified by using its intrinsic viscosity ($\eta$) at 25° C. orthochlorophenol, which is also more than 0.6 dl/g, preferably within the range of 0.8 to 0.85 dl/g.

The polyester resin mixture of which the tubular member is essentially made consists of the above-mentioned polyester resin mainly based on ethylene glycol and terephthalic acid at a rate of 5 to 95% in weight, preferably 50 to 90% in weight and the above-mentioned polyester resin mainly based on ethylene glycol and isophthalic acid at a rate of 95 to 5% in weight, preferably 50 to 10% in weight. It is preferable that the rate of the polyester resin mainly based on ethylene glycol and isophthalic acid is more than 20% in weight because superior gas barrier properties can be obtained. It is also preferable that the rate of the polyester resin mainly based on ethylene glycol and isophthalic acid is less than 50% in weight because the heat and shock resistances of the tubular member scarcely decreases. When the ratio of the polyester resin mainly based on ethylene glycol and isophthalic acid to the polyester resin mainly based on ethylene glycol and terephthalic acid is 30% in weight in the case that the polyester resin mainly based on ethylene glycol and isophthalic acid is mixed with pure polyethylene terephthalate (PET), double the gas barrier properties of the PET can be obtained. If the ratio of the polyester resin mainly based on ethylene glycol and isophthalic acid is too little, the aimed improvement cannot be attained. If the ratio is too much, affections of the polyester resin mainly based on ethylene glycol and isophthalic acid to the final product in brittleness and color become considerable. The ratio within the range of 10 to 50% in weight of the polyester resin mainly based on ethylene glycol and isophthalic acid to the polyester resin mainly based on ethylene glycol and terephthalic acid is preferable in view of the gas barrier and other physical properties. The more preferable range thereof is 20 to 35% in weight.

The above polyester resin mixture may be prepared by the manner that the polyester resin mainly based on ethylene glycol and terephthalic acid and the polyester resin mainly based on ethylene glycol and isophthalic acid are mixed with each other within the above-mentioned range by various known methods, for instance, using a Henschel mixer, a V-blender, a ribbon blender, a tumbler or the like. The resulting mixture may be kneaded with a single or twin screw extruder, a kneader, a Banbury mixer or the like. Granulation or mill techniques may also be used.

To the above polyester resin mixture, various additive agents generally used for polyester resin such as heat stabilizers, stabilizers for weather resistance, antistatic agents, lubricants, mold release agents, dispersants, pigments and dyes may be added within the scope of the present invention.

The tubular member 2 may be made of the above polyester resin mixture by injection molding, biaxial orientation, vacuum forming, compression molding or the like.

In the case of tubes for use in coagulating blood or counting red or white blood cells, it is preferable to treat the inner surface of the tubular member 2 to be hydrophilic so as to prevent blood cells from adhering to the inner surface. This treatment can be carried out by coating the inner surface of the tubular member 2 with hydrophilic materials such as water-soluble silicone resin, polyvinyl alcohol and polyvinyl pyrrolidone. An anticoagulant agent such as heparin powder and EDTA-2K may be applied to the inner surface of the tubular member 2 or contained in the tubular member 2. To the contrary, a blood-coagulation promoter may be applied to the inner surface of the tubular member 2 or contained in the tubular member 2.

As shown in FIG. 1, a coagulation promoter member 20 consisting of a film, a filter paper, a non-woven fabric or the like to which a blood-coagulation promoter has been applied or into which a blood-coagulation promoter has been permeated, may be enclosed in the tubular member 2. Instances of the blood-coagulation promoter are silica sands having particle diameters of 0.4 to 20 μm, crystal silica having particle diameters less than 5 μm and an average particle diameter of 1.1 μm (for instance, Min-U-Sil, the trade name of Pennsylvania Glass Sand Company), diatomite, fine glass particles, kaolin, bentonite, protamine sulfate and thrombin.

A serum separator may be contained in the tubular member 2. The serum separator is a thixotropic gel material having a specific gravity intermediate between those of serum and blood cell components to be examined. For instance, a material containing as the principal ingredients α-olefin-maleic diester copolymer to which modifiers for viscosity and specific gravity have been added, is usable for this purpose.

In the embodiment shown in FIG. 1, the closure member 3 comprises a gas-barrier member 4 having an adhesive film 6 disposed on the lower surface thereof and a sealing member 5 mounted on the upper surface of the gas-barrier member 4.

The gas-barrier member 4 is for hermetically closing the open end of the tubular member 2 to keep the interior of the tubular member 2 under reduced pressure. The gas-barrier member 4 comprises a gas-barrier film made of a material having high gas-barrier properties, for instance, a metal foil such as an aluminum foil or a resin such as ethylene-vinyl alcohol copolymer and polyvinylidene chloride. The adhesive film 6 is disposed on the lower surface of the gas-barrier member 4 for mounting the closure member 3 to the open end of the tubular member 2. The adhesive film 6 is made of a resin possible to be welded to the polyester resin of the tubular member 2 and having the ability of easy-peeling. The adhesive film 6 is preferably made of a modified polyester resin, which has a lower softening point than the polyester resin of the tubular member 2. The modified polyester resin should have good adhesion to polyethylene terephthalate and have moderate softening and glass transition points. It may consist of aromatic dicarboxylic acid such as terephthalic acid and isophthalic acid, and a diol such as ethylene glycol, 1,4-butanediol, diethylene glycol and neopentyl glycol. The modified polyester resin preferably has a softening point within the range of 80° to 170° C. (measured by the ring and ball method according to K2531 of the Japanese Industrial Standards) and a glass transition point within the range of −30° to 80° C. (measured by DSC method).

In the embodiment shown in FIG. 1, the closure member 3 is provided with a tab 9 for detaching the closure member 3 from the tubular member 2.

Figure 2:
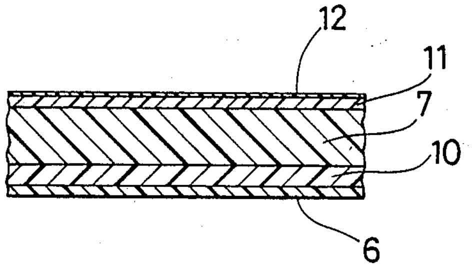
FIG. 2 is an enlarged fragmentary sectional view of a closure member of the blood collecting tube according to the present invention.

Referring next to FIG. 2, the gas-barrier member 4 is preferably provided with a resin film 10 disposed on the lower surface of the above-mentioned gas-barrier film, that is, between the gas-barrier film 7 and the adhesive film 6. This resin film 10 is for improving the mechanical strength of the whole film composite and may be made of an oriented PET film. A preferable form of the closure member 3 will be described. The closure member 3 comprises a gas-barrier film 7, a resin film 10 disposed on the lower surface of the gas-barrier film 7, and the adhesive film 6 disposed on the lower surface of the resin film 10. The closure member 3 may be provided with a printing layer 11 disposed on the upper surface of the gas-barrier film 7 for an indication of sort, etc. An overcoat 12 such as a cellulose coating layer may be provided to protect the printing layer 11.

The sealing member 5 should be of a material capable of sealing a puncture opening to maintain liquid-tightness both when the hollow needle segment of the tube holder or the like (not shown) is thrusted into and withdrawn from the closure member 3. The sealing member 5 may be made of rubber such as natural rubber, isoprene rubber, chloroprene rubber and silicone rubber, and a resin such as a thermoplastic elastomer, for instance, styrene-butadiene-styrene (SBS) block copolymer.

The shape of the sealing member 5 is as shown in FIG. 1, which has a plane bottom surface forming the adhesive surface to the gas-barrier member 4, and a recessed blood-receiving portion 13 formed at the upper center of the sealing member 5.

The blood-receiving portion 13 is for receiving and isolating blood which is adhered to the sealing member 5 when the hollow needle segment of the tube holder or the like is withdrawn from the closure member 3. The sealing member 5 is disposed substantially at the center of the upper surface of the gas-barrier member 4. The outline of the sealing member 5 may be one of circles and other circular shapes including ellipses, and polygons such as quadrangles and pentagons. Alternatively, the sealing member may cover the whole upper surface of the gas-barrier member 4. Although it is preferable to dispose the sealing member at the upper surface of the gas-barrier member 4, the sealing member may be disposed at the lower surface of the gas-barrier member 4.

The closure member 3 including the adhesive film as its lowermost layer can be attached in gas-tight manner to the flange 8 of the tubular member 2, or onto the fringe of the open end of the tubular member if such a flange is not provided, by welding with heat, ultrasonics or high frequency.

A conventional rubber plug may be used as closure member for the tubular member 2 instead of such a film-type closure member as described above.

A reduced-pressure state in the tubular member 2 can be established by the manner that the closure member 3 is attached to the tubular member 2 under reduced atmospheric-pressure.

An experiment for proving the effect of the invention will be described.

EXAMPLE

Tubular members used in the experiment had the shape as shown in FIG. 1 and the dimensions that the inner diameter at the open end, the thickness and the tapering rate were 13.4 mm, 1.0 mm and 15/1000, respectively. A flange having the outer diameter of 17.3 mm and the thickness of 2.0 mm was provided at the open end of every tubular member. Tubular members according to the invention were made by injection molding from a polyester resin mixture of polyethylene terephthalate (J025 available by Mitsui PET Corporation) and a polyester resin mainly based on ethylene glycol and isophthalic acid (B010; polyester copolymer consisting of terephthalic acid: isophthalic acid/ethylene glycol: 1,3-bis(2-hydroxy)benzene=10:90/85:15) where the polyethylene terephthalate resin: the polyester resin mainly based on ethylene glycol and isophthalic acid=7:3. They could be easily formed without whitening at the gate position and stopping-up of the gate of the injection molding machine. Every closure member used in the experiment comprised a gas-barrier member which was made of a film consisting of 12 μm PET (SPET available by Toyobo Co., Ltd.) as the uppermost layer, a 30 μm aluminum film as the intermediate layer, and a 15 μm modified polyester-coated PET film as the lowermost layer. The closure member was provided with a sealing member made of natural rubber and having the diameter of 7.0 mm and the thickness of 2.0 mm. A recess having the diameter of 3.0 mm and the depth of 0.8 mm was formed at the upper center of the sealing member.

A coagulation promoter-coated PET film (10 μm thick) was prepared by dipping a PET film into an ethanol solution in which crystal silca powder having an average particle diameter of 2 μm and polyvinyl pyrrolidone were dispersed. Coagulation promoter members each having the diameter of 11 mm were punched from the coagulation promoter-coated PET film.

Water-soluble silicone was sprayed to the inner surface of the tubular member so as to prevent blood clot from adhering. After inserting the coagulation promoter member, the tubular member was sealed with the closure member by the manner that the gas-barrier member of the closure member was welded to the tubular member with heat under reduced pressure. The above-mentioned sealing member was sealed on the upper surface of the gas-barrier member with adhesion. The blood-collecting tube thus obtained was regulated in its reduced internal pressure to be able to collect the initial amount of blood of 7.0 ml.

In this experiment, blood-collecting tubes sterilized by exposure to gamma radiations (1.5 Mrad) were also prepared. They, however, showed no difference in experimental results from those not sterilized.

COMPARATIVE EXAMPLE

For comparative examples, tubular members were made in the similar manner but using only polyethylene terephthalate (J025 available by Mitsui PET Corporation) instead of the above-mentioned polyester resin mixture. Blood-collecting tubes each of which was for collecting the initial amount of blood of 7.0 ml, were prepared using these tubular members in the same manner as those of the above-mentioned examples of the invention.

EXPERIMENT

When the change of the capability of collecting blood was observed at room temperature, the experimental results are shown in the following table 1, where the capability of collecting blood was measured by the manner that each tube was made to suck water, and the the measurement temperature and pressure were compensated.

TABLE 1

| Years | 0.5 | 1 | 1.5 | 2 |
|---|---|---|---|---|
| Example of invention | 6.7 ml | 6.5 ml | 6.3 ml | 6.1 ml |
| Comparative example | 6.5 ml | 6.1 ml | 5.7 ml | 5.4 ml |

Initialization: 7.0 ml

A blood-collecting tube of the present invention is advantageous because the interior of the tube can be thoroughly observed owing to no whitening upon injection molding as well as because the capability of collecting blood hardly decreases with time owing to its high gas barrier properties.

As many apparently widely different embodiments of this invention may be made without departing from the spirit and scope thereof, it is to be understood that the invention is not limited to the specific embodiment thereof except as defined in the appended claims.

What is claimed is:

1. A blood collecting tube comprising a tubular member made of synthetic resin which has an open end and a closed bottom, said tubular member having an inner surface, and a closure member which is for closing said open end of said tubular member to maintain a reduced pressure condition inside said tubular member and allows a puncture needle to pierce therethrough, said tubular member made of a mixture of (a) a first polyester resin comprising at least one dicarboxylic acid component and at least one glycol component, said first polyester resin mainly based on ethylene glycol as the glycol component and terephthalic acid as the dicarboxylic acid component and (b) a second polyester resin comprising at least one dicarboxylic acid component and at least one dihydroxy compound component, said second polyester resin mainly based on ethylene glycol as the dihydroxy component and isophthalic acid as the dicarboxylic acid component, and said mixture contains said first polyester resin mainly based on ethylene glycol and terephthalic acid in an amount of 5 to 95% by weight of said mixture.

2. A blood collecting tube according to claim 1, wherein said first polyester resin mainly based on ethylene glycol and terephthalic acid contains terephthalic acid components in an amount beyond 70 mol % of the whole dicarboxylic acid components thereof and ethylene glycol components in an amount beyond 70 mol % of the whole glycol components thereof, said second polyester resin mainly based on ethylene glycol and isophthalic acid contains isophthalic acid components in an amount of 20 to 100 mol % of the whole dicarboxylic acid components thereof, terephthalic acid components up in an amount up to 80 mol % of the whole dicarboxylic acid components thereof, ethylene glycol components in an amount of 10 to 95 mol % of the whole dihydroxy compound components thereof, and at least one dihydroxy compound component selected from the group consisting of 1,3-bis(2-hydroxyethoxy)benzene and 1,4-bis(hydroxyethoxy)benzene components, in an amount of 5 to 90 mol % of the whole dihydroxy compound components thereof.

3. A blood collecting tube according to claim 2, wherein said first polyester resin mainly based on ethylene glycol and terephthalic acid contains terephthalic acid components in an amount more than 90 mol % of the whole dicarboxylic acid components thereof.

4. A blood collecting tube according to claim 2, wherein said first polyester resin mainly based on ethylene glycol and terephthalic acid contains ethylene glycol components in an amount more than 90 mol % of the whole glycol components thereof.

5. A blood collecting tube according to claim 2, wherein said second polyester resin mainly based on ethylene glycol and isophthalic acid contains isophthalic acid components in an amount of 50 to 100 mol % of the whole dicarboxylic acid components thereof, and terephthalic acid components in an amount up to 50 mol % of the whole dicarboxylic acid components thereof..

6. A blood collecting tube according to claim 2, wherein said second polyester resin mainly based on ethylene glycol and isophthalic acid contains ethylene glycol components in an amount of 15 to 90 mol % of the whole dihydroxy compound components thereof, and at least one dihydroxy compound component selected from the group consisting of 1,3-bis(2-hydroxyethoxy)benzene and 1,4-bis(hydroxyethoxy)benzene components in an amount of 10 to 85 mol % of the whole dihydroxy compound components thereof.

7. A blood collecting tube according to claim 2, wherein said second polyester resin mainly based on ethylene glycol and isophthalic acid contains ethylene glycol components in an amount of 50 to 90 mol % of the whole dihydroxy components thereof and at least one dihydroxy compound component selected from the group consisting of 1,3-bis(2-hydroxyethoxy)benzene and 1,4-bis(hydroxyethoxy)benzene components in an amount of 10 to 50 mol % of the whole dihydroxy compound components thereof.

8. A blood collecting tube according to claim 1, wherein said first polyester resin mainly based on ethylene glycol and terephthalic acid is in an amount of 50 to 90% by weight of said mixture.

9. A blood collecting tube according to claim 1, wherein the inner surface of said tubular member is coated with a hydrophilic material.

10. A blood collecting tube according to claim 9, wherein the hydrophilic material is selected from the group consisting of water-soluble silicon resin, polyvinyl alcohol and polyvinyl pyrridone.

11. A blood collecting tube according to claim 1, wherein an anticoagulant agent is applied to the inner surface of said tubular member or contained in said tubular member.

12. A blood collecting tube according to claim 11, wherein the anticoagulant agent is heparin.

13. A blood collecting tube according to claim 1, wherein a blood-coagulation promoter is applied to the inner surface of said tubular member or contained in said tubular member.

14. A blood collecting tube according to claim 13, wherein the blood coagulation promoter is selected from the group consisting of silica sand having a particle diameter of 0.4 to 20 μm and crystal silica having a particle diameter less than 5 μm, diatomite, fine glass particles, kaolin, bentonite, protamine sulfate and thrombin.

15. A blood collecting tube according to claim 1, wherein said tubular member further comprises a flange at said open end thereof.

16. A blood collecting tube according to claim 1, wherein said closure member comprises a gas-barrier member having an upper surface and a lower surface, said gas-barrier member having an adhesive film disposed on said lower surface of said gas-barrier member and a sealing member disposed on said upper surface of said gas-barrier member.

17. A blood collecting tube according to claim 16, wherein said gas-barrier member comprises a gas-barrier film.

18. A blood collecting tube according to claim 17, wherein said gas barrier film is selected from the group consisting of aluminum foil, an ethylene-vinyl alcohol copolymer and polyvinylidene chloride.

19. A blood collecting tube according to claim 16, wherein said closure member further comprises a tab for detaching said closure member from said tubular member.

20. A blood collecting tube according to claim 16, wherein said sealing member has an upper surface having disposed thereon a recessed blood-receiving portion at the upper surface thereof.

21. A blood collecting tube according to claim 16, wherein the adhesive film comprises a modified polyester resin.

22. A blood collecting tube according to claim 21, wherein the adhesive film further comprises one or more of terephthalic acid, isophthalic acid, ethylene glycol, 1,4-butanediol, diethylene glycol and neopentyl glycol.

23. A blood collecting tube according to claim 1, wherein said closure member is welded to said tubular member.

24. A blood collecting tube according to claim 1, wherein said second polyester resin mainly based on ethylene glycol and isophthalic acid is in an amount of 95 to 5% by weight of said mixture.

25. A blood collecting tube according to claim 24, wherein said second polyester resin mainly based on ethylene glycol and isophthalic acid is in an amount of 50 to 10% by weight of said mixture.

26. A blood collecting tube according to claim 1, wherein the first polyester resin comprises polyethylene terephthalate and wherein the ratio of polyethylene terephthalate resin: the second polyester resin mainly based on ethylene glycol and isophthalic acid is 7:3.

27. A blood collecting tube according to claim 26, wherein the second polyester resin mainly based on ethylene glycol and isophthalic acid has the following composition: terephthalic acid: isophthalic acid/ethylene glycol: 1,3-bis(2-hydroxy)benzene=10:90/85:15.

28. A blood collecting tube according to claim 1, wherein the dicarboxylic acid component of said first polyester resin in addition to terephthalic acid comprises at least one acid selected from the group consisting of isophthalic acid, diphenylether-4,4-dicarboxylic acid, naphthalene-1,4-dicarboxylic acid, naphthalene-2,6-dicarboxylic acid, oxalic acid, succinic acid, adipic acid, sebacic acid, undeca-dicarboxylic acid and hexahydroterephthalic acid.

29. A blood collecting tube according to claim 1, wherein the glycol component of the first polyester resin comprises in addition to ethylene glycol at least one component selected from the group consisting of propylene glycol, 1,4-butandiol, neopentyl glycol, cyclohexane dimethanol and bisphenol.

30. A blood collecting tube according to claim 1, wherein a serum separator is contained in said tubular member.

31. A blood collecting tube according to claim 30, wherein the serum separator is an alpha-olefin-maleic diester copolymer.

* * * * *